United States Patent [19]

Charney

[11] 4,076,589
[45] Feb. 28, 1978

[54] PROCESS FOR THE PRODUCTION OF DIHYDROXYACETONE

[75] Inventor: William Charney, Montclair, N.J.

[73] Assignee: Schering Corporation, Kenilworth, N.J.

[21] Appl. No.: 596,935

[22] Filed: Jul. 17, 1975

Related U.S. Application Data

[63] Continuation-in-part of Ser. No. 364,771, May 29, 1973, abandoned.

[51] Int. Cl.² .............................................. C12D 1/10
[52] U.S. Cl. ...................................... 195/49; 195/100
[58] Field of Search ..................... 195/43, 49, 96, 30, 195/100, 101

[56] References Cited

PUBLICATIONS

Marini, "Transformation of Glycerol to Dihydroxyacetone by Acetobacter suboxydans", Chemical Abstracts, vol. 66, p. 4302, abs. No. 45471h (1967).
Gomercic et al., "Oxidation of Glycerol to Dihydroxyacetone by Acetobacter suboxydans", Chemical Abstracts, vol. 71, p. 122384, abs. No. 122377g (1969).
American Type Culture Collection Catalogue of Strains, 8th ed., (1968), pp. 134, 130, 152.
Batzing et al., "Biphasic Growth of Acetobacter on a Glycerol-Limiting Medium", Journal of Bacteriology, vol. 108, No. 1, pp. 592-595 (1971).

Primary Examiner—Raymond N. Jones
Assistant Examiner—Thomas G. Wiseman
Attorney, Agent, or Firm—Carver C. Joyner; Stephen B. Coan; Raymond A. McDonald

[57] ABSTRACT

Glycerol is efficiently converted to dihydroxyacetone by *Acetobacter suboxydans* at an acid pH under aerobic conditions in a medium consisting of yeast hydrolysate or fish hydrolysate, glycerol and water.

9 Claims, No Drawings

PROCESS FOR THE PRODUCTION OF DIHYDROXYACETONE

This application is a continuation-in-part of copending application Ser. No. 364,771 filed May 29, 1973, now abandoned.

This invention relates to a novel process for producing dihydroxyacetone by microbial fermentation. More particularly, this invention relates to the conversion, under controlled aerobic conditions, of glycerol to dihydroxyacetone by strains of *Acetobacter suboxydans*.

Prior Art

The scientific literature relating to the microbial conversion of glycerol to dihydroxyacetone is vast and sometimes contradictory. However, those describing processes which are purported to be commercially feasible usually employ a medium containing sources of inorganic ions such as alkali metal phosphates and sources of inorganic buffers such as alkaline earth metal carbonates; most frequently calcium carbonate. The buffers maintain the fermentation medium within a certain pH range which heretofore was believed to be critical. Although there appears to be little agreement in the art regarding the specific pH at which the process is best effected, it is generally agreed that the medium should be prevented from becoming too acid, e.g. below pH 5.0. In fact, studies conducted with *Acetobacter suboxydans* by F. Marini and reported in Annali di Microbiologia ed Enzimologia 15(6) pages 203–207 (1965) utilizing a fermentation medium consisting of potassium dihydrogen phosphate, brewers yeast, calcium carbonate, corn steep liquor, calcium pantothenate and doubly distilled glycerol gave maximum yields when *Acetobacter suboxydans* ATCC 621 was used with the foregoing materials. The studies led to the conclusion that:

"When the glycerol concentration is 110g/liter maximum yields are obtained by the addition of growth promoting substances (calcium pantothenate) to the fermentation medium".

The study also led to the conclusion that,

"in order to obtain high conversion yields the pH of the culture must be buffered by adding fixed amounts of calcium carbonate to the fermentation medium, the optimum pH being 5.3–4.4".

The studies also indicated that a temperature above or below 30° C adversely affected the yield of dihydroxyacetone.

Another similar prior art process employs corn steep liquor, urea and glycerol and to obtain yields of 95%–96% after 96 hours fermentation. This process is effected without buffers, the final pH being about 3.7.

DESCRIPTION OF THE INVENTION

Contrary to the teaching of the prior art including those described hereinabove, I have discovered that using *Acetobacter suboxydans*, especially *Acetobacter suboxydans* ATCC 621, glycerol may be converted to dihydroxyacetone in high yield using a single nutrient. Further, I have discovered that the conversion may be effected in the absence of growth promoters, such as calcium pantothenate; and in the absence of buffers, such as calcium carbonate; and in the absence of alkali metal phosphates. Moreover I have discovered that the conversion may advantageously be effected at lower pH ranges than the prior art would suggest.

Thus, the invention sought to be patented in its process aspect resides in a method for producing dihydroxyacetone which comprises cultivating *Acetobacter suboxydans* under submerged aerobic conditions in a nutrient medium consisting of glycerol, water and yeast hydrolysate or fish hydrolysate at a pH from about 3.3 to 4.3 and at a temperature of from about 27° C to about 33° C for from about 24 to about 46 hours and separating the dihydroxyacetone so produced from said medium.

More specifically, the invention sought to be patented is a process which comprises cultivating *Acetobacter suboxydans* ATCC 621 under aerobic conditions in a nutrient medium containing glycerol, yeast hydrolysate or fish hydrolysate and water at a pH in the range of from about 3.3 to 4.3. Advantageously, the process is effected under conditions wherein the glycerol is present at from about 5% to about 15%, preferably from about 9% to about 12% (weight to volume), the yeast hydrolysate or fish hydrolysate being present at from about 0.2% to about 1.0% (weight to volume) with about 0.5% being preferred.

The fermentation is complete in from about 24 to about 48 hours, usually in about 30 hours. The product is isolated by methods known in the art, such as, filtration of the whole broth, removal of inorganic cations and/or anions (when present) via ion exchange resin adsorption, concentration of the resin effluent and crystallization of the dihydroxyacetone from the concentrate. Other methods of isolating dihydroxyacetone using ion exchange resins are known in the art such as those described by Liebster et al. of the *Biological Institute* (Prague) in Chemicke Listy 50 (1956), pages 395–397.

Yeast hydrolysate is sometimes referred to as yeast extract depending upon the name preferred by the vendor of the material. It is generally prepared by the action of proteolytic enzymes upon the yeast, the particular enzymes those naturally present in yeast. These products are usually rich in nitrogen containing nutrients such as, amino acids and peptones. Exemplary of such products are Amber BYF 50 and Amber BYF 100 (Amber Labs. Milwaukee, Wisconsin) or Staley's Vico D150 (A. E. Staley Manufacturing Company, Decatur, Illinois).

Additionally, fish hydrolysates such as Vanco Fish Peptone (Van Camp Labs., Terminal Island, California) or Haynie Dried Fish Peptone (Haynie Products Inc., Baltimore, Maryland) may also be utilized as nutrients for this process. In general, the various products are equivalents for the instant process. However, Ardamine-Z ®, sold by Yeast Products Inc., Paterson, New Jersey, is the nutrient preferred by applicants.

Where the concentrations of glycerol and yeast or fish hydrolysate are set forth, it is to be understood that unless the contrary is expressly stated, weight to volume of fermentation medium is intended.

As is the general rule in microbiological transformations, the instant process is initiated by the preparation of an inoculum which is generally prepared in two or more stages. The initial stage in this process is one wherein the microorganism is permitted to grow on the surface of a nutrient medium at about 25°–30° C, preferably 28° C for about 3 days without agitation. Generally, the inoculum is prepared in a medium consisting of yeast hydrolysate (0.5%), potassium dihydrogen phosphate (0.1%) glycerol (6.0%) and water. The second stage is usually effected by transferring the first stage inoculum into about 20 volumes of fresh, sterile medium with agitation at about 28° C for from about 48 to about 72 hours or until the density of the culture when measured on a Klett turbidometric device reaches about 250–260. At this junction, the fermentation may be commenced by transferring under aseptic conditions with agitation and aeration 5% (by volume) of the inoculum into sterile fermentation medium. The fermentation is complete in from about 24 to about 48 hours, usually about 30 hours. The end-point of the fermentation may be determined by methods known in the art. I prefer to sample the fermentation medium at about 3 hour intervals after the first 12 hours. The samples are chromatographed on silica gel plates against dihydroxyacetone and glycerol using a solvent system consisting of chloroform, methanol, and water in the volume ratio of 80:19:1. The plates are then exposed to iodine vapors and sprayed with a reagent containing a mixture of the following ingredients: 3 g. phosphomolybdic acid, 45 ml. of methanol, 45 ml. of distilled water and 10 ml. of concentrated sulfuric acid. Heating of the plates at 100° –140° C for a few minutes gives rise to dark spots against a white background. The reference spots have the following $R_f$ values: glycerol 0.32 and dihydroxyacetone 0.55.

When the fermentation is complete, the only spot observed by this technique coincides with the dihydroxyacetone reference spot.

The isolation technique found by applicant to be most convenient utilizes cationic and anionic exchange resins for removal of impurities found in the fermentation. These impurities for the most part are derived from the nutrient materials. If permitted to remain, they interfere with the isolation of the product.

The ion exchange resins preferred by applicant are the Amberlites produced by Rohm and Haas, Philadelphia, Pennsylvania. The preferred cationic resin is Amberlite IRC-120, the preferred ionic resin being Amberlite IRA-401S which also serves a decolorizing function. The procedure for isolating the dihydroxyacetone generally employed by the applicant is as follows: Using a suitable filter aid, (e.g. high flow super-cel-Johns Manville, Inc.) filter the whole broth to remove insolubles. Pass the filtrate through a suitable cation exchange resin column and wash the resin column with deionized water. Pass the effluent and wash through a suitable anion exchange resin column (in the citrate cycle) and wash the column with deionized water. Combine the effluent and wash from the column and concentrate in vacuo keeping the temperature at or below 40° C to aproximately 10% of the original whole broth volume. With agitation add an equal volume of n-butanol. Water is removed from the mixture via vacuum distillation with the addition of n-butanol followed by concentration of the n-butanol to yield dihydroxyacetone as a white crystalline solid. Yields are usually in the range of from about 75 to about 90% by weight based upon the glycerol charge. Thin layer chromatography using the above-described technique shows one shot corresponding to dihydroxyacetone.

The fermentation should be "worked up" as promptly as possible after completion, it being known that Acetobacter is capable of converting dihydroxyacetone to by-products causing a concomitant reduction in the yield of dihydroxyacetone obtained.

The following examples are set forth to show the best mode for practicing this invention. It is known that many variations and combinations may be employed to perform substantially the same fermentation. Applicants consider those variations and combinations to be within the scope of their invention.

EXAMPLE I

Inoculum Preparation

A. First Stage
Medium:
0.5% yeast extract
0.1% potassium dihydrogen phosphate
6.0% glycerol
100 ml. soft water Prepare a series (e.g. 10) flasks of inoculum using 300 ml. Erlenmeyer flasks. Sterilize the medium at 121° C for 30 minutes. Inoculate the sterile medium under aseptic conditions with a loopful of *Acetobacter suboxydans* ATCC 621 and incubate under static conditions at 28° C for from about 48 to about 72 hours.

B. Second Stage
Medium:
0.5% Ardamine Z
0.5% potassium dihydrogen phosphate
6.0% glycerol
500 ml. soft water Sterilize a series of flasks containing the second stage medium in 2 liter Erlenmeyer flasks at 121° C for 40 minutes and after cooling to 28° C, add 5.0% (v/v) of the first stage inoculum to the sterile medium. Incubate the flasks at 28° C on a rotary shaker at from about 280 to about 320 rpm. for 48 hours, at which time the turbidometric reading (Klett) is about 250 to 260.

| Medium | Fermentation | |
|---|---|---|
| Ardamine Z | 0.45 | kg. |
| Glycerol | 9.9 | kg. |
| Soft Water | 90 | liters |
| Antifoam (GE-60) | 50 | ml. |

Prepare the fermentation medium in a 25 gal. (working volume) agitated fermentor. Sterilize the medium for 45 minutes at 121° C. Adjust the pH of the sterile medium to about 3.7 using 12N sulfuric acid. Cool the fermentation medium to about 30° C and inoculate with 5.0 liters of the second stage inoculum. Aerate the fermentation mixture at about 3.5 cu. ft/min. while agitating at about 350 rpm adding antifoam as required. Maintain the temperature at about 30° C and the pH range of 3.3 to 4.3. Monitor the utilization of the glycerol by thin layer chromatography. Stop the fermentation when the glycerol is completely utilized and isolate the dihydroxyacetone by the usual procedure

EXAMPLE 2

| Medium | Fermentation | |
|---|---|---|
| Ardamine Z | 50 | gm. |
| Glycerol | 1.1 | kg. |
| Soft Water | 10 | liters |
| Antifoam (GE-60) | 5 | ml. |

Charge the fermentation mediumto a 14 liter agitated fermentor equipped for aeration. Adjust the pH of the medium to 4.0 using 12N sulfuric acid and sterilize for 45 minutes at 121° C. Cool the fermentor to 30° C and add 500 ml. of second stage inoculum, prepared as described in Example 1. Set the agitator for 800 rpm and the aeration for 8 liters/minute. Maintain the temperature at about 30° C and the pH between 3.5 and 4.4. Monitor the utilization of the glycerol by thin layer chromatography and, when the fermentation is complete, isolate the dihydroxyacetone promptly.

By replacing Ardamine Z with an equivalent quantity of fish hydrolysate, such as, Vanco fish peptone or Haynie dried fish peptone and by following the process of Example 2, dihydroxyacetone may also be produced.

In a similar manner, by replacing Ardamine Z with an equivalent quantity of other yeast hydrolysate, such as, Amber BYF-50, Amber BYF-100 or Staley's Vico D-150, dihydroxyacetone may also be produced. Applicant considers the utilization of such nutrients within the scope of his invention.

EXAMPLE 3

Isolation of Dihydroxyacetone

To 2 liters of fermentation mixture from Example 2, add 22 g. of filter aid and 22 g. barium carbonate with stirring. Stir for about 15 minutes and filter through a clarifying mat precoated with 22 g. of filter aid. Prepare an ion exchange resin column (approximately one inch I.D.) containing 140 ml. of strongly acidic cation exchange resin in the hydrogen (preferably Amberlite IRC-120) cycle. Pass the filtrate through the resin column at a rate of about 25 – 30 ml. per minute. Wash the column with about 140 ml. of deionized water and combine the eluate and wash. Prepare an anion exchange resin column of approximately 220 ml. (preferably Amberlite IRA-401S) in the citrate cycle. Pass the combined eluate and wash from the previous column through the resin column at approximately 20-25 ml. per minute, wash the column with approximately 220 ml. of deionized water and combine the wash with the eluate. Concentrate the combined wash and eluate in vacuo to a volume of approximately 220 ml. keeping the temperature at or below 40° C.

To the 220 ml. of concentrated eluate, add 440 ml. of n-butanol and remove the water by azeotropic distillation in vacuo at or below 40° C. The complete removal of water may be determined by the refractive index of the distillate. Stir the crystalline slurry at room temperature for approximately 16–20 hours. Filter and wash the crystalline solid with chilled (0° C) acetone and dry at or below 40° C. Yield 176 g. (two fractions equaling approximately 80% weight based upon glycerol charge).

I claim:

1. A method for producing dihydroxyacetone which comprises cultivating *Acetobacter suboxydans* under submerged aerobic conditions for from about 24 to about 48 hours in a fermentation medium consisting of water, from about 5% to about 15% of glycerol, from about 0.2% to about 1.0% of a single nutrient selected from the group consisting of yeast hydrolysate and fish hydrolysate at a temperature of from about 27° C to about 33° C, at a pH from 3.3 to 4.3 wherein said percentages are weight to volume, and isolating the dihydroxyacetone therefrom to obtain thereby from about 75 to about 90% by weight based upon the glycerol added.

2. A method according to claim 1 wherein yeast hydrolysate is employed.

3. A method according to claim 1 wherein fish hydrolysate is employed.

4. A method according to claim 2 wherein the yeast hydrolysate is present at a concentration of 0.5%.

5. A method according to claim 3 wherein the fish hydrolysate is present at a concentration of 0.5%.

6. A method for producing dihydroxyacetone according to claim 4 which comprises cultivating *Acetobacter suboxydans* ATCC 621 under submerged aerobic conditions for from about 24 to about 48 hours in a fermentation medium consisting of water, from about 9% to about 12% of glycerol, 0.5% of yeast hydrolysate, at 30° C and at a pH from about 3.3 to 4.3.

7. A method according to claim 5 which comprises cultivating *Acetobacter suboxydans* ATCC 621 under submerged aerobic conditions for from about 24 to about 48 hours in a fermentation medium consisting of water, from about 9% to about 12% of glycerol, 0.5% of fish hydrolysate, at 30° C, and at a pH from about 3.3 to 4.3.

8. A process according to claim 6 wherein the medium contains 11% of glycerol.

9. A process according to claim 7 wherein the medium contains 11% of glycerol.

* * * * *